United States Patent [19]

Khoobehi et al.

[11] Patent Number: 5,976,502
[45] Date of Patent: Nov. 2, 1999

[54] METHOD OF VISUALIZING PARTICLES AND BLOOD CELLS CONTAINING A FLUORESCENT LIPOPHILIC DYE IN THE RETINA AND CHOROID OF THE EYE

[75] Inventors: Bahram Khoobehi, Metairie; Gholam A. Peyman, 123 Walnut St., New Orleans, both of La. 70118

[73] Assignee: Gholam A. Peyman, New Orleans, La.

[21] Appl. No.: 08/954,969

[22] Filed: Oct. 21, 1997

[51] Int. Cl.⁶ ............................. A61K 49/00; A61B 5/00
[52] U.S. Cl. ........................... 424/9.6; 600/310; 600/317
[58] Field of Search ............................. 424/9.6, 9.1, 9.8, 424/450, 489; 600/317, 558, 431, 310; 351/206, 200; 356/51

[56] References Cited

U.S. PATENT DOCUMENTS

| | | | |
|---|---|---|---|
| 3,893,447 | 7/1975 | Hochheimer et al. | 600/431 |
| 4,125,320 | 11/1978 | Rassow et al. | 351/13 |
| 4,409,979 | 10/1983 | Roussel et al. | 128/303.1 |
| 4,499,897 | 2/1985 | Roussel | 128/303.1 |
| 4,520,816 | 6/1985 | Schachar et al. | 128/303.1 |
| 4,762,701 | 8/1988 | Horan et al. | 424/1.1 |
| 5,394,199 | 2/1995 | Flower | 351/206 |
| 5,437,274 | 8/1995 | Khoobehi et al. | 128/633 |

OTHER PUBLICATIONS

"An In Vitro Model of the Kitten Retinogeniculate Pathway", Guido et al., The American Physiological Society, 1997.

"Lipophilic Tracers—DiI, DiO, DiD and DiA", Product Information Sheet, Molecular Probes, 1996.

"DiI and DiO: Versatile Fluorescent Dyes for Neuronal Labelling and Pathway Tracing", Honig et al., Trends in Neurosciences, Sep. 1989.

"Fluorescent Carbocyanine Dyes Allow Living Neurons of Identified Origin to be Studied in Long–Term Cultures", Honig et al., Journal of Cell Biology, vol. 103, Jul. 1986, 171–187.

*Primary Examiner*—Jose' G. Dees
*Assistant Examiner*—Michael G. Hartley
*Attorney, Agent, or Firm*—Roylance, Abrams, Berdo & Goodman, L.L.P.

[57] ABSTRACT

A method for detecting blood flow in the retina and choroid uses a scanning laser ophthalmoscope and a lipophilic fluorescent dye contained in carrier. The fluorescent dye in one embodiment is able to fluoresce in the visible and near infrared spectral range. The carrier can alternatively contain dye that fluoresces in the visible range and a dye that fluoresces in the infrared spectral range. The fluorescent dye enables the carrier to be visualized in the retina and the choroid.

14 Claims, 1 Drawing Sheet

METHOD OF VISUALIZING PARTICLES AND BLOOD CELLS CONTAINING A FLUORESCENT LIPOPHILIC DYE IN THE RETINA AND CHOROID OF THE EYE

FIELD OF THE INVENTION

The present invention is directed to a method observing a carrier and monitoring blood flow in the retina and choroid. More particularly, the invention is directed to a method of visualizing, imaging and recording the presence and movement of a carrier and fluorescent dye in blood vessels through the eye.

BACKGROUND OF THE INVENTION

The measurement of blood flow and blood velocity in vessels is an important diagnostic tool for determining blockage in the vessel as well as other vascular disorders. Measurement of retinal blood flow is particularly valuable for providing information relating to circulation of blood through the numerous submicron size blood vessels in the eye. Retinal vascular disorders can be diagnosed by monitoring blood flow through the retina.

A number of methods of measuring vascular blood flow and in particular retinal blood flow use a fluorescent dye, such as fluorescein, which can fluoresce when exposed to light within a narrowly defined wavelength. The fluorescent dye is injected into the blood stream in a predetermined site. A sharp, easily visible wavefront of the dye, referred to as a bolus, is obtained by controlling the injection of the dye in the vessel. A bolus cannot be obtained repeatedly because the previously injected dye accumulates in the vessel and causes background interference thereby preventing precise identification of the bolus. Another disadvantage of injecting the dye directly into the bloodstream is that the concentration of the dye is diluted as the dye passes through the different vessels. As the dye is diluted, the bolus is more difficult to detect. Furthermore, a bolus in micro-circulation, such as that in the optic nervehead, cannot be readily detected.

Efforts to overcome some of the deficiencies of injecting dyes directly into the bloodstream include the use of lipid vesicles to encapsulate the dye. The lipid vesicles have also been used to encapsulate drugs. The lipid vesicles can be injected into the bloodstream where they rupture to release the encapsulant, designated areas of the body can be subjected to microwave or laser energy causing the lipid vesicles to rupture. One example of releasing drugs or other encapsulants by subjecting a designated area of the body to laser energy to rupture the encapsulant is disclosed in U.S. Pat. No. 4,891,043 to Zeimer et al.

Numerous devices have also been developed to observe the fundus of the eye. Many of these fundus cameras require high light intensities which result in ocular damage. To overcome the risk of damage caused by high intensity light, laser scanning techniques have been employed. An example of a digital laser scanning fundus camera is described in Plesch et al., Digital Laser Scanning Fundus Camera, *Applied Optics,* Vol. 26, No. 8, pp. 1480–86, Apr. 15, 1987. This device uses a collimated laser beam focused by the eye to a spot of 10–15 microns diameter for illumination of a single point of the retina. The light scattered back from the retina, normally 3–5% of the incident light, is collected through the outer 95% of the pupil. Angular scanning of the illuminating laser beam sweep the spot across the retina and results in time resolved sequential imaging of the retina. The device is connected to a digital image buffer and a microcomputer for image storage and processing.

The above noted methods of introducing fluorescent dyes into the bloodstream have experienced some success in producing images of blood vessels and determining blood flow and blood velocity. These methods do not always produce accurate measurement of blood flow in the retinal macrocirculation and macular microcirculation. Furthermore, these methods are not able to measure blood flow in the small vessels of the optic nervehead. There is, therefore, a continuing need in the art for a method of directly and accurately measuring and detecting blood flow in the optic nervehead, retinal microcirculation around the macula, retinal macro circulation of the major vessel and choroid.

SUMMARY OF THE INVENTION

Accordingly, a primary object of the invention is to provide a method of observing blood flow in the eye and particularly in the choroidal and retinal vessels.

Another object of the invention is to provide a method of staining blood cells with a lipid soluble fluorescent dye and fluorescing and visualizing the stained blood cells in the choroid and retina of the eye.

A further object of the invention is to provide a method of fluorescing stained blood cells by a laser beam in the infrared spectral range.

Another object of the invention is to provide a method visualizing and observing blood cells in the choroid where the blood cells are stained with a lipid soluble carbocyanine dye capable of fluorescing in the infrared spectral range and in the visible spectral range.

The objects of the invention are basically attained by providing a method of observing a carrier in the blood of an eye at a specific site in the eye comprising the steps of incorporating a dye in a lipid vesicle, microcapsule, manocapsule or blood cell carrier, said dye being capable of fluorescing when exposed to the infrared and blue-green part of the electromagnetic spectrum, injecting the carrier into the blood stream of an animal to carry the carrier through the blood vessels in the retina and choroid in the eye, generating a laser beam from a scanning laser ophthalmoscope, the laser beam having a wavelength in the blue-green or infrared part of the spectrum capable of fluorescing the dye, applying the laser beam to the carrier located at the retina and choroid to fluoresce the dye, and visualizing and observing the carrier in the retina and choroid.

The foregoing objects are also attained by providing a method of observing blood flow in the choroid of an eye, comprising the steps of staining blood cells with a carbocyanine dye capable of fluorescing in the infrared part of the electromagnetic spectrum, injecting the blood cells into the blood stream in the eye of an animal, focusing a laser beam from a scanning laser ophthalmoscope on the choroid of the animal to fluoresce the dye in the blood cells, the laser beam having a wavelength in the infrared electromagnetic spectral range, and visualizing and observing the stained blood cells and observing blood flow in the choroid.

The objects of the invention are further attained by providing a method of observing blood flow in the retina and choroid of an eye comprising the steps of: staining blood cells with at least one first carbocyanine dye capable of fluorescing in the visible spectral range, staining said blood cells with at least one second carbocyanine dye capable of fluorescing in the red or infrared spectral range, introducing said stained blood cells into the blood stream of an eye to enable said cells to flow through the retina and choroid, generating a first laser beam from a scanning laser ophthalmoscope and focusing the laser beam on the retina, wherein said first laser beam is in the visible spectral range to excite said dye and visualize said blood cells in the retina, and generating a second laser beam from a scanning laser ophthalmoscope and focusing the laser beam on the choroid, wherein said second laser beam is in the red or infrared spectral range to excite said second dye and to visualize said blood cells in the choroid.

Other objects advantages and salient features of the invention will become apparent from the following detailed description of the invention, which in conjunction with the annexed drawing discloses preferred embodiments of the invention.

BRIEF DESCRIPTION OF THE DRAWING

Referring to the drawing which forms a part of this disclosure in which.

DETAILED DESCRIPTION OF THE INVENTION

Figure 1:
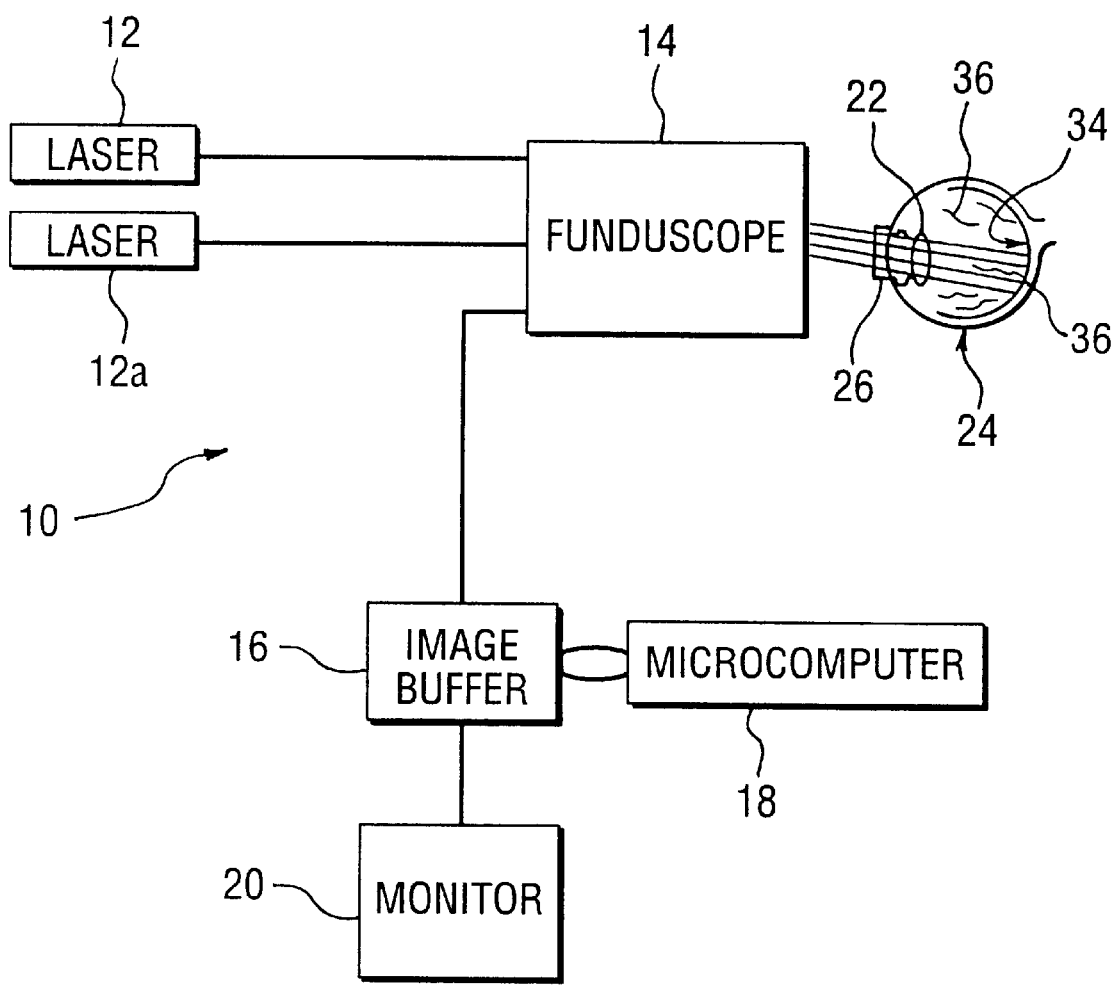
FIG. 1 is a schematic diagram of the system in accordance with the invention shown in use with the eye and comprising a laser, a system for delivering, observing and recording the laser light, and a microcomputer for coordinating the recording system.

The invention is directed to a method of observing blood flow through the eye by injecting a carrier containing a fluorescent carbocyanine dye into the blood stream in the eye of an animal. The carbocyanine dye can be water soluble or lipid soluble. In embodiments, the dye is a lipophilic carbocyanine dye that fluoresces in the visible and/or infrared electromagnetic spectrum. The carrier containing the dye is injected into the blood stream of the subject animal. A laser beam is focused onto the retina or choroid to excite and fluoresce the dye so that the carrier can be visualized and observed in the eye. The dye-labeled carrier is observed and the fluorescence recorded as the carrier travels through the blood stream to provide diagnostic information including the presence of artery blockage or restrictions, blood flow rates and blood flow velocity.

The method of the invention incorporates a fluorescent dye into a carrier such as blood cells, liposomes, nanocapsules and microcapsules. The carrier is dispersed to form a suspension and injected into the blood stream to flow through the predetermined target site. The concentration of the carrier in the suspension and the amount of the suspension injected into the blood stream will depend on the specific site, the carrier and the amount of dye incorporated into the carrier. The carrier contains a sufficient concentration of the dye so that the carrier can be visualized and observed when the dye fluoresces. A laser beam is then produced having a wavelength complementing the dye so that the dye fluoresces when exposed to the laser. The laser is focused to the target site in the eye where the dye fluoresces when the carrier passes through the blood vessels in the target site. The target site can be, for example, the vessel in the optic nervehead, choroidal vessel, retinal micro or macro vessel.

In a preferred form of the invention, the carrier contains a carbocyanine dye such as a lipophilic carbocyanine dye that fluoresces in the blue-green or red electromagnetic spectrum and in the infrared spectrum. In this manner, the dye in the carrier can be observed and visualized in the retina and the choroid blood vessels. The retina is transparent to the blue-green and red spectrum so that a fluorescing dye in the visible spectrum can be visualized in the retina. The choroid is impermeable to the blue-green laser light so that the dye in the choroid will not fluoresce and therefore cannot be visualized when exposed to a laser beam in the visible, blue-green spectrum. By focusing a red or an infrared laser beam on the choroid, the red or infrared light is able to pass through the tissue of the choroid and excite the dye in the carrier in the blood vessels of the choroid. The fluorescing dye in the carrier then can be visualized and observed in the choroid.

The lipophilic carbocyanine dye in further embodiments of the invention is able to fluoresce when exposed to a laser beam in the visible range and also in the near infrared range. The carrier containing the carbocyanine dye is injected into the blood stream to flow through the eye. The laser beam is focused on the retina to project a visible laser beam to fluoresce the dye in the carrier in the retina. The visible laser beam can then be interrupted or turned off and a second laser energized to project a red or infrared laser beam onto the surface of the eye to penetrate the choroidal tissue and fluoresce the dye in the carrier in the choroid. In this manner the blood flow rate in the retina and the choroid can be measured using a single dye or a single injection of the particulate carrier. In addition, the carrier and the dye passing through the retina can be readily distinguished from the carrier and dye passing through the choroid since the visible laser beam is able to fluoresce only the dye in the retina.

In further embodiments, a mixture of a first carrier containing a dye capable of fluorescing when exposed to a laser beam in the visible range and a second carrier containing a dye capable of fluorescing when exposed to a red or infrared laser beam is injected into the blood stream to flow into the eye. A laser beam in the visible range, red or infrared range can be selected and focused on the eye to selectively visualize and observe the fluorescing carrier in the retina or the choroid. Alternatively, the carrier can contain a mixture of dyes where at least one dye fluoresces in the presence of a laser beam in the visible range and at least one dye fluoresces in the presence of a laser beam in the red or infrared spectral range.

In preferred embodiments, the carrier is blood cells that have been stained with the carbocyanine dye and particularly lipophilic carbocyanine dyes. Live blood cells are preferred to avoid introducing foreign particles into blood stream. Stained blood cells continue to fluoresce for at least about two hours and as long as 24 hours. The carrier can be whole blood or isolated white blood cells, red blood cells or platelets. The blood cells are stained by mixing a lipophilic dye with the blood sample and incubating for about 15 minutes to allow the lipophilic portion of the dye to bind with the lipid layer of the cell membrane. Initially, the dye is dissolved in DMSO (dimethyl sulfoxide) or ethanol. Then the blood cells are typically mixed with a 1% solution of the dye. Generally, a 10 ml blood sample is sufficient to obtain an adequate volume for injecting into the blood stream. The excess dye is then washed away and the stained cells are recovered. The cells can be dispersed in a suitable stabilizing solution and injected into the blood stream. Other standard cell staining procedures can be used as known in the art. In further embodiments the lipophilic dye is introduced directly into the blood stream where the dye attaches to the lipid layer of the cell membrane.

The cells can be stained with a single dye or a mixture of different dyes. In one embodiment, the cells can be stained with two lipophilic dyes where the first dye fluoresces when exposed to a red or infrared laser beam and a second dye fluoresces when exposed to a laser beam in the blue-green spectral range. The cells are stained by both dyes so that the dyed cells are able to fluoresce when exposed to either laser. Alternatively, two blood cell samples can be stained with different dyes and the stained blood cells mixed together prior to injecting into the blood stream.

The lipophilic carbocyanine dyes have the general formula

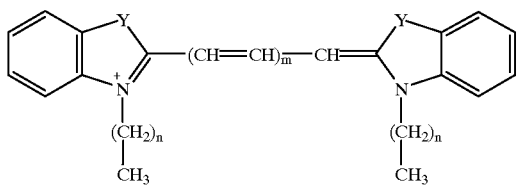

where Y is oxygen, sulfur, methylene
or isopropyl,
m is 1-3, and
n is 12-22.

The dye compounds are generically referred to by the designation DiI where Y is isopropyl and DiO where Y is oxygen. The compounds are more specifically referred to by the formula $DiYC_{n+1}$ (2m+1). Examples of suitable carbocyanine dyes are commercially available from Molecular Probes, Inc., Eugene, Oreg.

In preferred embodiments, the dye is able to fluoresce in the presence of an argon laser, a helium-neon laser or an infrared laser. For example, a dye sold under the tradename D-275 by Molecular Probe, Inc. fluoresces green when exposed to an argon laser at 484 nm. The dye sold under the tradename D-1121 fluoresces orange when exposed to a long wavelength laser at 560–574 nm. A preferred infrared excitable dye is $DiIC_{18}(7)$ which fluoresces at about 740–780 nm.

The dye is contained in the carrier in a concentration sufficient to fluoresce when exposed to the laser beam and to enable to carrier to be visualized by the ophthalmoscope. The carrier can be dispersed in a suitable carrier fluid or introduced directly into the blood stream. The carrier containing the dye is injected into the blood stream proximate the target site in the eye, such as the saphenous vein, to allow the carrier to flow through the retina.

In further embodiments of the invention, the lipophilic dye is entrapped in lipid vesicles or liposomes. As known in the art, liposomes are vesicles made from phospholipids defining a lipid phase encapsulating an aqueous phase. The lipophilic dye is preferably incorporated into the lipid bilayer of the liposome. The liposomes can be prepared from a phospholipid, such as, for example, dipalmitoyl-phosphatidylglycerol (DPPG) and dipalmitoylphosphatidyl-choline (DPPC). The lipid wall can be strengthened when needed by the use of cholesterol in the lipid phase to prevent leakage of the lipid wall. The phospholipids used to encapsulate the dye can have a transition temperature below 37° C., such as phosphatidylcholine. In embodiments, the phospholipids have a transition temperature below 37° C. by using the phospholipid in combination with cholesterol. The liposomes preferably have a size of about 0.02 to 2.0 microns and preferably less than 1.0 micron. When the phospholipids have a transition temperature above 37° C., the cholesterol is generally not necessary.

The liposomes are prepared by standard procedures as known in the art. For example, the lipophilic carbocyanine dye can be dispersed in the phospholipid and mixed with the aqueous phase. The organic phase is then removed from the mixture and the resulting lipid vesicles are recovered. The fluorescent dye is contained in the liposomes in the amount of about 0.2–2.0 mmol. to avoid quenching the dye. In embodiments, the concentration of the dye can be sufficiently high to quench the fluorescent properties of the dye. In this embodiment, the walls of the liposomes are sufficiently permeable to permit some of the dye to diffuse outward. As the dye diffuses outward, the lipophilic dye adheres to outer surface of the lipid bilayer at a concentration to fluoresce when subjected to the laser beam.

The liposomes can be unilamellar or multilamellar made by known procedures. Suitable procedures are disclosed in U.S. Pat. No. 4,235,871 to Papahadjapoulos et al. and U.S. Pat. No. 4,522,803 to Lenk et al.

The nanocapsules are also prepared according to conventional procedures as known in the art. These nanocapsules comprise a liquid or solid core encapsulated by a continuous wall of a water insoluble membrane of a synthetic polymer. The nanocapsules have a size of about 0.1–0.4 microns. The nanocapsules may be prepared, for example, by the process described in Fessi et al., Nanocapsule Formation by Interfacial Polymer Deposition Following Solvent Displacement, *International Journal of Pharmaceutics*, 55 (1989) R1–R4. The process includes dissolving a known amount of poly, (D,L lactide) polymer in acetone. A known amount of a phospholipid is dissolved in acetone by heating close to the boiling point. An aqueous solution of a fluorescent dye is then added to the acetonic solution. The resulting organic solution is poured into a known amount of water containing poloxamer while stirring. The poloxamer is a highly water soluble surfactant needed for physical stability of the nanocapsule suspension. The acetone rapidly diffuses toward the aqueous phase and is removed under reduced pressure. The resulting colloidal suspension if concentrated to the desired final volume by the removal of water. In alternative processes, the nanocapsules may be prepared from other polymers such as polyvinylacetate, polyvinylchloride, poly E-caprolactone and ethylcellulose.

Microspheres and nanospheres are formed from polymers and copolymers forming an encapsulating outer wall and an aqueous or other liquid core or a solid core. Microspheres are 2.0–4.0 microns, while nanospheres are less than 1.0 micron. The microspheres in preferred embodiments have a diameter of up to about 2.0 microns. Suitable polymers include, for example, polylacetic acid, polyglycolic acid and copolymers, thereof, ethylene-vinyl acetate, polyanhydrides, polyamides, and orthoesters. The microcapsules may be prepared according to known methods, such as the methods disclosed in U.S. Pat. No. 4,997,652 to Wong and Bindschaedler et al., Polyanhydride Microsphere Formulation by Solvent Extraction, Journal of Pharmaceutical Sciences, Vol. 77, no. Aug. 8, 1988.

Referring to FIG. 1, the scanning laser funduscope or ophthalmoscope 10 includes a laser 12, a scanning projector and photomultiphier and focusing system 14, an image buffer system 16, a microcomputer 18 and a monitor 20. The system used in preferred embodiments of the invention combines a very sensitive high resolution laser scanning imaging procedure and a means to digitally manipulate the raw image from the laser scanner. Advantageously, the laser delivery system is a laser scanning funduscope using a collimated laser beam focused by the eye to a spot of 10–15 microns in diameter for illumination of a single point on the retina. The light scattered back from the retina is about 3–5% of the incident light and is collected through the outer 95% of the pupil. The illuminating laser beam sweeps the spot across the retina by angularly scanning of the laser resulting in time resolved sequential imaging of the retina. The resolution of the image is determined by the illumination and sensitivity of the detection pathways. Advantageously, the laser delivery system and observing and recording means is a laser scanning fundus camera substantially as shown in FIG. 1 and described in Plesch et al., Digital Laser Scanning Fundus Camera, Applied Optics, Vol. 26, No. 8, Apr. 15, 1987 and U.S. Pat. No. 5,177,511 to Manfred et al., and in U.S. Pat. No. 5,437,274 to Khoobehi et al. which are incorporated by reference. A laser scanning ophthalmoscope which can be effectively used in practicing the invention is manufactured by G. Rodenstock Instrumente GmbH and sold by Rodenstock USA, Inc. Medical Division of Danbury, Conn.

The laser delivery system is schematically illustrated in FIG. 1. In the embodiment illustrated the system includes two lasers 12, and 12a which can be selectively actuated. The laser 12 preferably produces a laser beam in the visible spectral range while laser 12a produces a laser beam in the red or infrared range. Laser 12 can be, for example, an argon laser capable of producing several lines in the blue and blue-green spectral range such as a model 162A from Spectra-Physics, Inc. Alternatively, laser 12 can be a helium-neon laser capable of producing a laser beam in the red spectral range. Laser 12a is a laser which produces a laser beam in the near infrared range of about 700 nm to about 3,000 nm. The laser beam is delivered to the target site at an intensity to fluoresce the dye without rupturing or damaging the carrier or damaging the tissue in the target site. The normal operating intensity is a few microwatts as is routinely used in clinical angiography. This produces a dim, continuous laser beam which scans through the fundus.

The illuminating laser beam passes through an electrooptic modulator to provide intensity control of the scanning beam. The beam then passes through two microscope objectives for beam shaping and through a mechanical shutter.

The illuminating beam is then horizontally deflected by a rotating eighteen-facet polygon mirror. The mirror is rotated by a motor at about 52,100 rpm to produce a fast linear scan with a repetition rate of 15.625 Khz corresponding to the closed circuit television standard. The effective angular beam deflection is 30° with a system time-out of 20% of a line scan time. A suitable eighteen-facet mirror is produced by Lincoln Laser Co.

The illuminating beam exiting the polygon mirror scanner is passed through a confocal arrangement of two camera lenses to magnify the beam by a factor of two. A linear galvanometer scanner deflects the illuminating beam vertically with a repetition rate of 50 Hz and a flyback time of two minutes. A second symmetrical arrangement of two camera objectives projects the laser beam via a semi-transparent mirror of low reflectivity into the eye. The overall beam has a waist of about 2 nm in diameter at the pupil plane which is the conjugate of the two scanning planes.

The lens 22 of the eye 24 focuses the illuminating beam to form a raster in the photoreceptor plane within the retina if refraction is normal. Refraction deviation of three diopters shift the plane of focus about 1 mm off the retina. It is preferable to prefocus the beam to keep the plane of focus within the retina. A contact lens 26 may be used to focus the laser.

The light reflected from the fundus and exiting the eye passes through the semi-transparent mirror, an aspheric ophthalmic lens and a photomultiplier tube. The light is then collected by an observation and recorder device. A polarizing beam splitter and a second photomultiplier tube are provided for simultaneous two-channel polarization imaging. The semitransparent mirror passes 70% of the incident light.

The optical image from the eye is received by the photomultiplier tubes and converted to an electronic time-resolved signal. The signal is then transferred to an image buffer 16 after a change of impedance and preamplification of the signal. In the image buffer 16, the signal is digitized, stored and visualized as a color coded image reconstruction on a monitor screen 20.

An important aspect of the scanning laser is the control of the system timing and synchronization of the scanner motion detector recording and image buffer timing. The image buffer system 16 is used as the base for synchronizing the scanner and the recording system. The image buffer 16 transmits signals to the motor controller to control the speed of the motor.

The precise orientation of the scanning mirrors is determined by a He—Ne laser projected to the rotating mirror and a photodiode. A photodiode transmits signals to the image buffer 16 corresponding to the laser pulses from the laser 12. Thus, each sweep of the mirror produces two signals which are fed to the image buffer 16.

The image buffer 16 is coupled to a microcomputer 18 such as a MC68000-based Eodata 3300 microcomputer where the recorded images are digitally stored on a disk or further processed as desired.

The result of the delivery system and recording system is to produce a digitized image having a high resolution. Although the laser scanning fundus camera cannot ordinarily detect particles having a size of less than 10 microns, it has been found that the encapsulated fluorescent dye when subjected to the laser light of the appropriate wavelength fluoresces to visualize the particles individually in the blood stream. A digitized image is produced which enables the movement of the individual particles through the blood vessel. In the case of examining the retina 34 of the eye, the movement of the fluorescing carrier particles or vesicles can be traced from the point they enter the arteries 36 and travel to capillaries until they exit the retina through the veins. The velocity of blood in retinal vessels is determined by the time period that the particle spends travelling through the vessel and the length of the vessel. Since the carrier is not ruptured in the blood stream, the method can be repeated without interference from the previous injection.

The scanning laser fundus camera is advantageous since it is able to detect fluorescing particles of 0.02 to 10 microns while passing through a vessel. The movement of each individual fluorescing carrier is easily visualized so that the elapsed time and distance that the carrier travels is easily measured. Since the image is digitized, a video tape can be replayed one frame at a time for accurate measurement of the time and distance traveled by the carrier. The microcomputer can be used to overlay a multiple of video frames on a single image and thus produce a visible path of the carrier. The known magnification of the video can be used to determine the actual length of the path. The velocity of blood flow is thus obtained by dividing the distance traveled by the elapsed time.

The system according to the invention is particularly advantageous for use in producing an image of the retina. The small particles containing the incorporated or encapsulated fluorescent dyes having a size of less than 1.0 micron and which can pass through the small vessels can be visualized when the dye is fluoresced. This allows imaging of blood flow and measurement of blood flow in retinal macrocirculation, the macular microcirculation, optic nerve-head having a 10 micron arteriole microcirculation and in choroidal vessels. The scanning laser ophthalmoscope is able to detect and track the location of the carrier at any given time.

While several advantageous embodiments have been disclosed to illustrate the invention, it will be understood by those skilled in the art that various changes and modifications can be made therein without departing from the scope of the invention as defined in the appended claims.

What is claimed is:

1. A method of observing a carrier in the blood stream in an eye at a specific site, comprising the steps of incorporating a dye in a lipid vesicle, microcapsule, or nanocapsule carrier, said dye fluorescing when exposed to infrared and the visible parts of the electromagnetic spectrum, injecting the carrier into the blood stream of an animal to carry the carrier through blood vessels in the retina and choroid of an eye;

generating a first laser beam from a scanning laser ophthalmoscope, said first laser beam having a wavelength in the visible part of the electromagnetic spectrum which fluoresces said dye;

applying the first laser beam to the carrier located at the retina to fluoresce said dye in said retina without fluorescing said dye in said choroid and visualizing the carrier in the retina;

generating a second laser beam having a wavelength in the infrared part of the electromagnetic spectrum from a scanning laser ophthalmoscope;

applying the second laser beam to the carrier in the choroid to fluoresce said dye in the choroid, and visualizing and observing the carrier in the choroid.

2. The method of claim 1, wherein said dye is a lipid soluble carbocyanine dye.

3. The method of claim 2, wherein said dye is DiI or DiO.

4. The method of claim 2, wherein said carbocyanine dye is $DiIC_{18}(7)$ and has an excitation wavelength of about 740 to 780 nm.

5. A method of observing a carrier in the blood stream of an eve comprising incorporating a first carbocyanine dye into a lipid vesicle, microcapsule or nanocapsule carrier and injecting the carrier into the bloodstream to pass through the blood vessels in the retina and choroid, wherein said first dye fluoresces when exposed to a laser beam in the visible spectral range;

incorporating a second carbocyanine dye into a lipid vesicle, microcapsule or nanocapsule carrier, and injecting the carrier into the bloodstream to pass through the blood vessels in the retina and choroid, wherein said second dye fluoresces when exposed to a laser beam in the infrared spectral range;

generating a first laser beam from a scanning laser ophthalmoscope in the visible part of the electromagnetic spectrum;

generating a second laser beam from a scanning laser ophthalmoscope in the infrared part of the electromagnetic spectrum;

applying the first laser beam to the carrier located at the retina to fluoresce said first dye and visualizing the carrier in the retina without fluorescing the carrier in the choroid;

applying the second laser beam to the carrier in the choroid to fluoresce said second dye and visualizing the carrier in the choroid.

6. The method of claim 5, wherein said first dye fluoresces in the blue-green spectral range and said method comprises applying a laser beam from an argon laser onto said retina to fluoresce said dye.

7. The method of claim 5, wherein said first dye fluoresces in the red spectral range and said method comprises applying a laser beam from a helium-neon laser onto said retina to fluoresce said dye.

8. The method of claim 5, wherein said second dye fluoresces at about 740–780 nm when exposed to an infrared laser, said method further comprising focusing said infrared laser on the choroid of the eye to fluoresce said second dye in the choroid.

9. The method of claim 1, further comprising sequentially applying a visible laser beam to the retina to fluoresce said dye in the carrier and visualize the carrier in the retina, and applying an infrared laser beam to the choroid to fluoresce said dye in the carrier and visualize the carrier in the choroid.

10. A method of observing blood flow in the retina and choroid of an eye comprising the steps of staining blood cells with at least one first carbocyanine dye fluorescing in the visible spectral range;

staining said blood cells with at least one second carbocyanine dye fluorescing in the infrared spectral range;

introducing said stained blood cells into the blood stream of an eye to enable said cells to flow through the retina and choroid;

generating a first laser beam from a scanning laser ophthalmoscope and focusing the laser beam on the retina, wherein said first laser beam is in the visible spectral range to excite said first dye and visualize said blood cells in the retina substantially without exciting said second dye in the choroid; and discontinuing said first laser beam and generating a second laser beam from a scanning laser ophthalmoscope and focusing the laser beam on the choroid, wherein said second laser beam is in the infrared spectral range to excite said second dye and to visualize said blood cells in the choroid.

11. The method of claim 10, comprising introducing at least one of said dyes into the blood stream and staining said blood cells in the blood stream.

12. The method of claim 10, wherein said blood cells are selected from the group consisting of red blood cells, white blood cells and platelets.

13. The method of claim 10, wherein said first dye fluoresces in the presence of an argon laser beam or helium-neon laser beam.

14. The method of claim 10, wherein said second dye fluoresces when exposed to a laser beam at about 740–780 nm.

* * * * *